(12) United States Patent
Meyer (10) Patent No.: US 9,398,970 B1
(45) Date of Patent: Jul. 26, 2016

(54) ROOSTER BOOT ANKLE FOOT ORTHOSIS

(75) Inventor: Grant C. Meyer, Muskegon, MI (US)

(73) Assignee: Grant C. Meyer, Muskegon, MI (US)

( * ) Notice: Subject to any disclaimer, the term of this patent is extended or adjusted under 35 U.S.C. 154(b) by 1322 days.

(21) Appl. No.: 12/658,427

(22) Filed: Feb. 5, 2010

(51) Int. Cl.
*A61F 5/00* (2006.01)
*A61F 5/01* (2006.01)

(52) U.S. Cl.
CPC .................................... *A61F 5/0111* (2013.01)

(58) Field of Classification Search
CPC ... A61F 5/0111; A61F 5/0113; A61F 5/0102; A61F 5/01; A61F 5/0127; A61F 2005/0134; A61F 2005/0132; A61F 2005/0137; A61F 2005/0146; A61F 2005/0158; A61F 2005/0165; A61F 2005/0179; A61F 2005/0148
USPC ........................... 602/27, 23, 28, 16; 128/882
See application file for complete search history.

(56) References Cited

U.S. PATENT DOCUMENTS

| | | | |
|---|---|---|---|
| 4,669,142 A | 6/1987 | Meyer | |
| 4,756,096 A | 7/1988 | Meyer | |
| 4,934,355 A * | 6/1990 | Porcelli | 602/16 |
| 5,036,837 A | 8/1991 | Mitchell et al. | |
| 5,044,360 A | 9/1991 | Janke | |
| 5,358,469 A | 10/1994 | Patchel et al. | |
| 5,429,588 A | 7/1995 | Young et al. | |
| 5,486,157 A | 1/1996 | Dibenedetto | |
| 5,542,912 A * | 8/1996 | Hess | 602/27 |
| 5,611,773 A * | 3/1997 | Nash et al. | 602/16 |
| 5,749,840 A | 5/1998 | Mitchell et al. | |
| D395,514 S | 6/1998 | Stano | |
| 6,824,523 B2 | 11/2004 | Carlson | |
| 6,860,864 B2 | 3/2005 | Meyer | |
| 7,101,346 B1 | 9/2006 | Davis | |
| 7,182,743 B2 | 2/2007 | Slautterback et al. | |
| 2005/0070834 A1 | 3/2005 | Herr | |

OTHER PUBLICATIONS

Dynamic Splint Systems, Inc (www.Dynasplint.com)—Web Site AD "Dorsiflexion & Plantar Flexion Dynasplint Systems for the Ankle".
Dynamic Splint Systems, Inc. (www.Dynamicsplint.com)—Web Site Ad "Dorsiflexion & Plantar Flexion Dynasplint Systems for the Ankle".

* cited by examiner

*Primary Examiner* — Victoria J Hicks
(74) *Attorney, Agent, or Firm* — Gardner, Linn, Burkhart and Flory, LLP (57) ABSTRACT

The Rooster Boot is a lightweight therapeutic ankle foot orthosis designed for increasing the range of motion and correcting alignment of the foot and ankle. The dynamic orthosis creates a variable load stretch at the ankle to prevent contracture and shortening of the heel cord. The orthosis is utilized during rest, sleep, and weight bearing therapy. This dynamic design has been of particular benefit to children with spasticity or weakening muscles, as evidenced in cerebral palsy.

19 Claims, 7 Drawing Sheets

ROOSTER BOOT ANKLE FOOT ORTHOSIS

BACKGROUND OF THE INVENTION

1. Field of the Invention

The present Rooster Boot invention relates to an ankle foot orthosis designed for increasing the range of motion and correcting the alignment of a patient's foot and ankle. The applicant's novel dynamic orthosis creates a variable load stretch at the ankle to prevent contracture of the heel cord. The orthosis is utilized during rest, sleep, and weight bearing therapy. An adjustable power pack assembly provides the necessary force to bring the foot into a dorsi flexed position.

This dynamic design has been of particular benefit to children with spasticity or weakening muscles (these conditions are often seen in cerebral palsy and with muscle weakness. The child patients are generally confronted with muscle imbalance. Their muscles do not work together as normal children's do. Their spasticity, or weakness makes some muscles overpower other muscles, and create unwanted pulls or forces on their joints. This imbalance of muscle pulls, can create contracture and misalignment of involved joints and related structures. If this misalignment is not corrected, it will eventually lead to permanent deformity in the child, or planter flexion distorsion in the heel cord (Achilles Tendon).

Planter flexion is a normal position when the foot is flexed downward. A spastic contracture of the posterior tibial muscles (calf), can hold the foot in that position and produce a shortening of the heel cord (Achilles Tendon). This type of positioning can also be seen when there is a weakening in the anterior muscles below the knee. This shortened heel cord can generate additional undesirable positions, which can lead to permanent deformity if not treated.

2. Description of the Related Prior Art

The prior art relates generally to conventional static orthosis support systems that are rigid and inflexible while limiting the motion. They are often restrictive and cumbersome to the patient.

Even the dynamic prior art has inherent design flaws, causing the ankle and foot orthosis boot devices to be both heavy and cumbersome to the patient wearer, while providing limited monitoring control and adjustment.

By contrast the Rooster Boot is light weight, non-cumbersome, and provides circumferential support and dynamic stabilizing forces. It will provide range of motion improvements for dorsiflexion, as well as preventing spastic contracture shortening of the heel cord, which can lead to deformity.

The novel adjustable lock feature of the subject invention provides the practitioner the ability to adjust the range of motion in both dorsi and planter flexion. No other prior art orthotic device provides the unique features of the subject Rooster Boot ankle foot orthosis, in a simplified, and lightweight functional design.

U.S. Pat. Nos. 5,036,837; 5,749,840 to Mitchell, et al.; and U.S. Pat. No. 5,358,469 to Patchel, et al. teach and describe an adjustable heavy and cumbersome adjustable coiled leaf spring pivotal joint dynamic splint with adjustable elongated strut assemblies that is excessively bulky for the boot patient wearer, and is not designed for ambulation.

Similarly, Patent Application number 20050070834 to Herr, Blaya, and Pratt describes an active ankle foot orthosis to treat ankle foot gait pathology used for foot drop. It incorporates a heavy, bulky, and expensive design with torsional springs, and spring damper positional control. Application number 20050070834, does not teach nor describe the applicant's novel invention.

U.S. Pat. No. 5,044,360 to Janke teaches and describes sets of cam members in matching pairs used interchangeably for controlling range of motion in plantar flexion and dorsiflexion. It does not have an adjustable force mechanism to provide stretch as in the applicants invention, and does not claim the applicants Rooster Boot novel features.

U.S. Pat. No. 5,486,157 to DiBenedetto teaches and describes, but does not claim an elastic strap. Also, it does not provide the adjustable lock assembly mechanism for the range of motion control in dorsi and planter flexion.

U.S. Pat. No. 7,101,346 B1 to Davis teaches and describes a dynamic response ankle-foot orthosis with laminating mechanical joints to the medial and lateral aspects of a brace, and providing cutouts in the lamination just anterior and posterior to the ankle joint axis of motion. It does not teach nor claim the adjustable lock range of motion in dorsi and planter flexion, of the subject patent application.

U.S. Pat. No. 7,182,743 B2 to Slautterback et al teaches and describes a foot splint to provide for maintaining a wearer's foot and his plantar fascia, in preselected dorsiflexion, providing for restful sleep, but does not address the dynamic range of motion features of the subject invention to prevent contracture.

SUMMARY OF THE INVENTION

The present Rooster Boot Invention overcomes the disadvantages of the prior art static and dynamic orthosis by providing a lightweight boot for the patient to wear at night while asleep and at rest to increase his range of motion in dorsi and planter flexion. The Rooster Boot has a mid-sole and sole for weight bearing therapy. The Rooster Boot is designed to provide adjustable and dynamic stretch load to the posterior muscles and heel cord to help prevent contracture and shortening of the heel cord. The novel design of the Rooster Boot provides total contact for pressure reduction while maintaining correct alignment.

The Rooster Boot promotes a low-load stretch during rest and sleep to improve the patient's range of motion. The Rooster Boot foot section is pulled up in dorsiflexion toward the tibia by forces from the adjustable power pack assembly, with adjustable means provided by the power pack assembly, including; a tension adjuster, tension gauge with numerical indicia gradations, and power band segment further disposed with a slot and anchor pin at the lower end. The tension adjuster is further disposed with a threaded barrel insert at its upper end with a threaded bolt for insertion into the tension adjuster and is also provided with an anchor pin at its upper end.

The adjustable locking plate assembly provides the ability to monitor and adjust the range of motion in dorsi and planter flexion, and also provides the patient care giver a numerical readout for indicating the patient's progress. The lightweight locking plate assembly is further provided with a micro-fine screw adjustment with a numerical monitoring range readout to a preferred dorsiflexion, planter flexion, or locked position at or near 90 degrees.

Upon weight bearing, the power pack assembly may be adjusted to relieve all tension on the foot of a child patient. The ROM (range of motion) can be monitored during various standing positions whereby the patients weight provides a ground reaction control by the pretibial shell. The forward flexion of the tibia and lower leg can be stopped at the desired position by the adjustable lock mechanism and pretibial shell. As the lower leg flexes at the ankle towards the foot, the tibia rotates medially. During weight bearing, the pretibial shell and posterior shell force the lower leg in the proper position for positive aligned support of the patient. A tongue extension of the pretibial shell is provided to position the the Rooster Boot on the patient, and Velcro, or other strap means is provided to secure the boot to the patient.

A variable dynamic passive stretch works comfortably preventing contracture, increasing ROM (range of motion), and correcting alignment of tissues below the knee. The Rooster Boot can be utilized during sleep, as well as weight bearing physical therapies.

Locking, or stopping the ankle motion at the various positions with the adjustable locking plate assembly, will result in ground reaction forces sent to the pretibial shell. These forces may be beneficial and studied for enhancing weight bearing support at standing and ambulation. A further Rooster Boot optional design variation could include (2) sets of adjustable power pack and locking plate assemblies, set in the 90 degree upright position for improved stability and torsional rigidity.

BRIEF DESCRIPTION OF THE DRAWINGS

FIG. 1 shows a perspective assembled view of the Rooster Boot orthosis including: a pretibial shell and tongue assembly (2); pretibial shell liner (1); in the lower front portion of said Rooster Boot; Velcro straps (3); a posterior shell (4) in the upper back portion of said Rooster Boot; an adjustable power pack assembly (5) further including; a tension adjuster (6) with an upper portion having numerical readout gradations, and a threaded receiving bore (7), and Allen-head threaded bolt (8), engaging said power pack assembly (5), and said receiving bore (7); and a lower portion further including; a power band segment (18) having a slotted end (12), further disposed with an engagement pin (13), movable within the slotted end (12), of said adjustable power band segment (18); and wherein said power pack assembly (5), and attachment of the power band and tension adjuster parts are also secured by fasteners (9); and a footshell liner (19) with a midsole and sole.

A critical and unique design feature of the Rooster Boot as further shown in FIG. 1, reveals a slotted plate assembly (10), that further includes a locking pin (14), and an adjustable slot (11), with variable predetermined slot engagement positions for locking in place with locking pin (14). The slot (11) includes ends configured to stop movement of pin (14) at the various engagement positions, including: a dorsi flexion positive angle forward position, variable (+ or −) 90 deg slot position; and an upper planter flexion position of said locking plate assembly slot (11).

FIG. 7 further displays the numerical readout gradations (17), for the said screws (16) micro-fine variable engagement position of said locking pin (14), for the variable positions within the slot.

DETAILED DESCRIPTION OF THE PREFERRED EMBODIMENT

Figure 1:
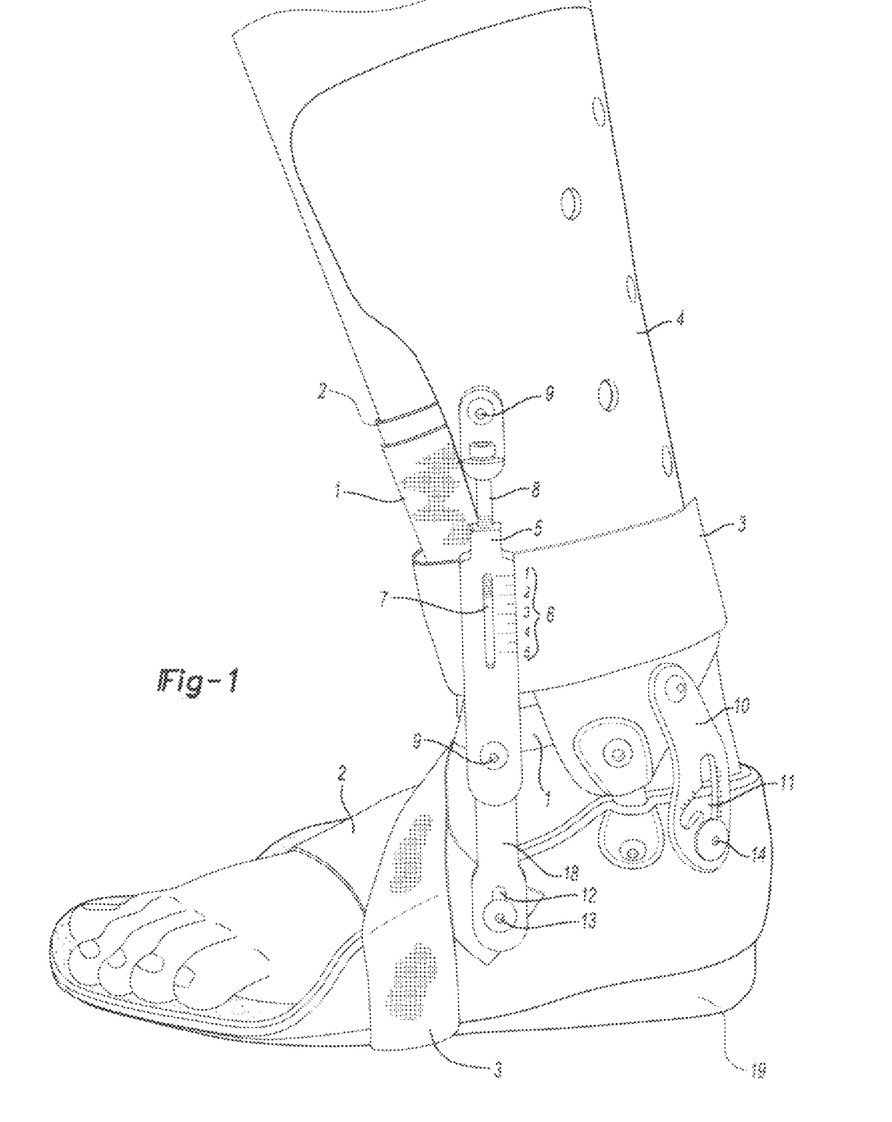

The preferred embodiment of the applicant's novel Rooster Boot design features would comprise: the pre-tibial shell (1), and posterior shell (4), and foot shell with liner (19), with a mid sole and sole, as depicted and described in FIG. 1, with optional additional second Velcro strap (3); further including the novel features of the adjustable power pack assembly (5) having an upper portion disposed with a tension adjuster segment having numerical readout gradations (6), and disposed with a threaded bore to receive a threaded Allen-head bolt (8) that is configured to be rotated in the threaded bore (7); and a lower portion with a slotted end of said power pack assembly (5), power band segment (18), slidably engaged within slot (12), with anchor pin (13).

Figure 2:
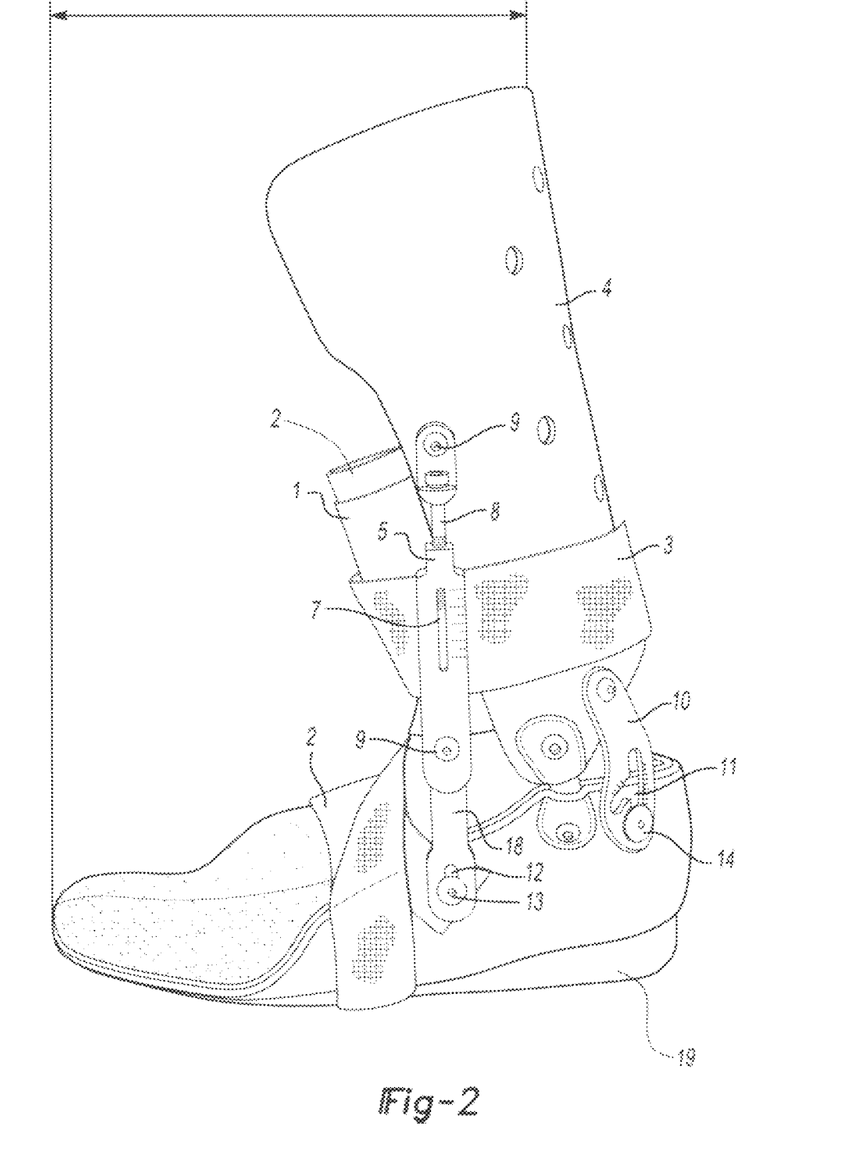
FIG. 2 shows the Rooster Boot orthosis, as described in FIG. 1, wherein the adjustable slotted locking plate assembly (10), slot (11), and engagement pin (14) are in the dorsi flexion position (ie: raised toe front portion of said boot), in the bottom portion of said slot (11).
Figure 3:
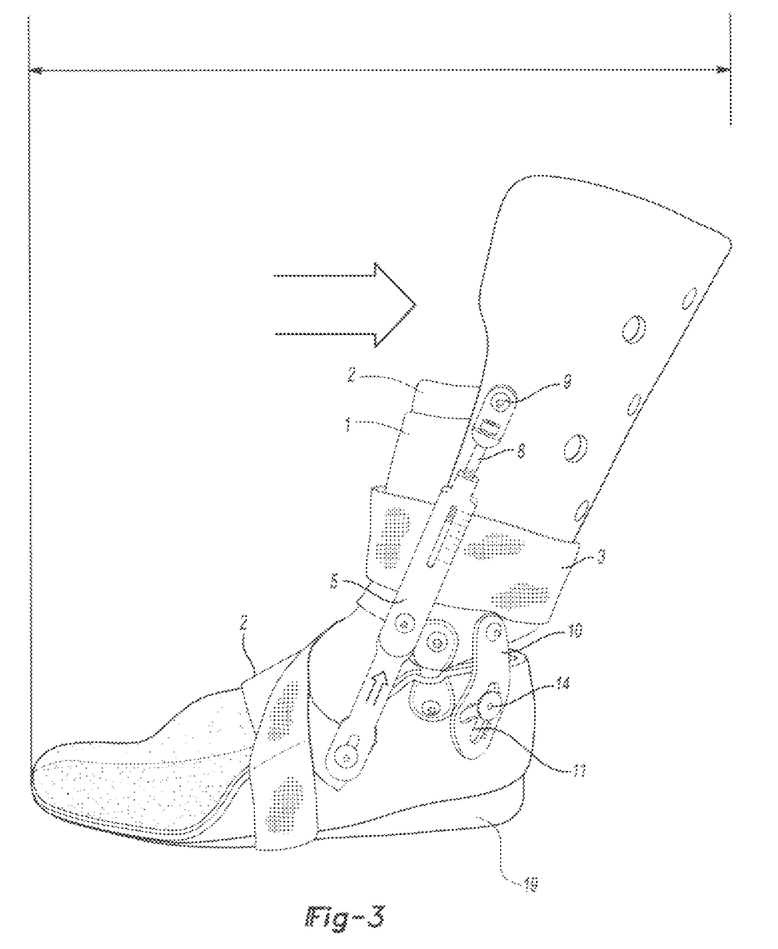
FIG. 3 provides an illustration showing the Rooster Boot orthosis in the planter flexion position of slot (11), with the engagement pin (9), slideably moved upward toward the top upper portion of the slot (11), of said adjustable locking plate assembly (10); and wherein, said pretibial shell (1), and posterior shell (4) is tilted, as indicated by the arrow in negative position toward the upper stop of the slot (11), in a planter flexion position, and wherein the adjustable power pack assembly (5), is in the fully stretched and extended position.
Figure 4:
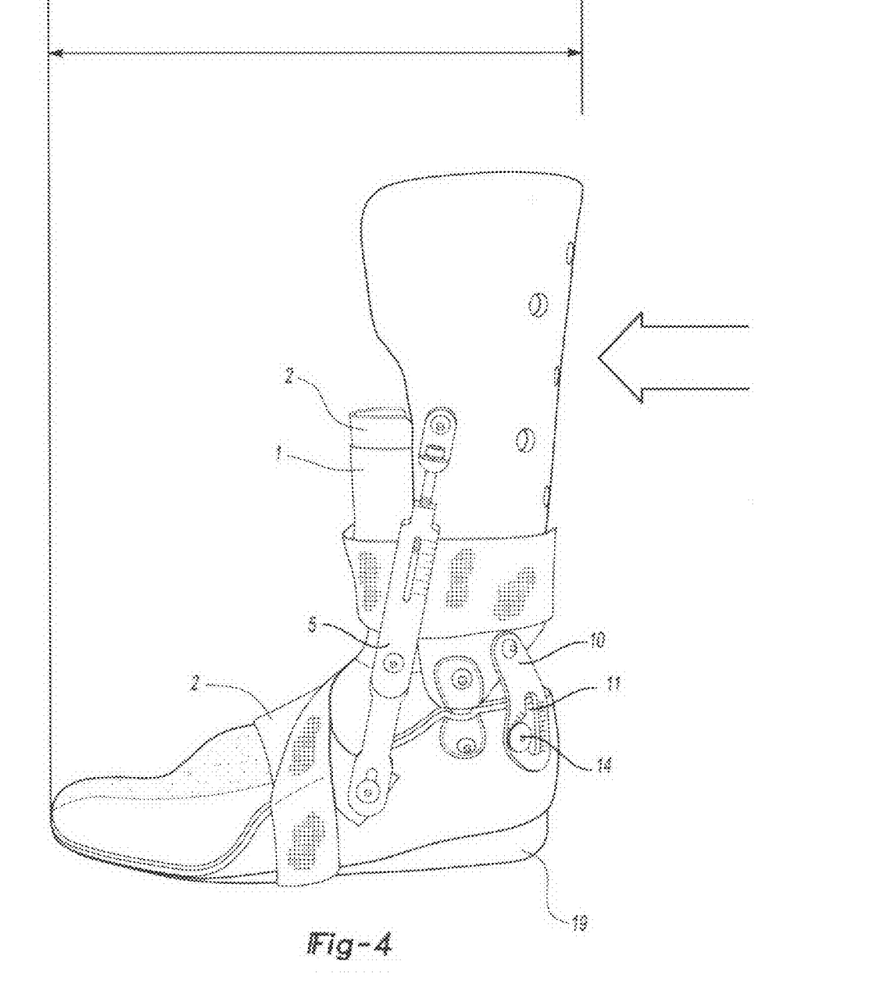
FIG. 4 shows the Rooster Boot in the 90 deg locked position with said adjustable locking assembly (10), slot (11), and locking engagement pin (14) in the 90 degree position in said slot (11). The power pack assembly (5), is then shown in its 90 deg respective position alignment with said boot.
Figure 5:
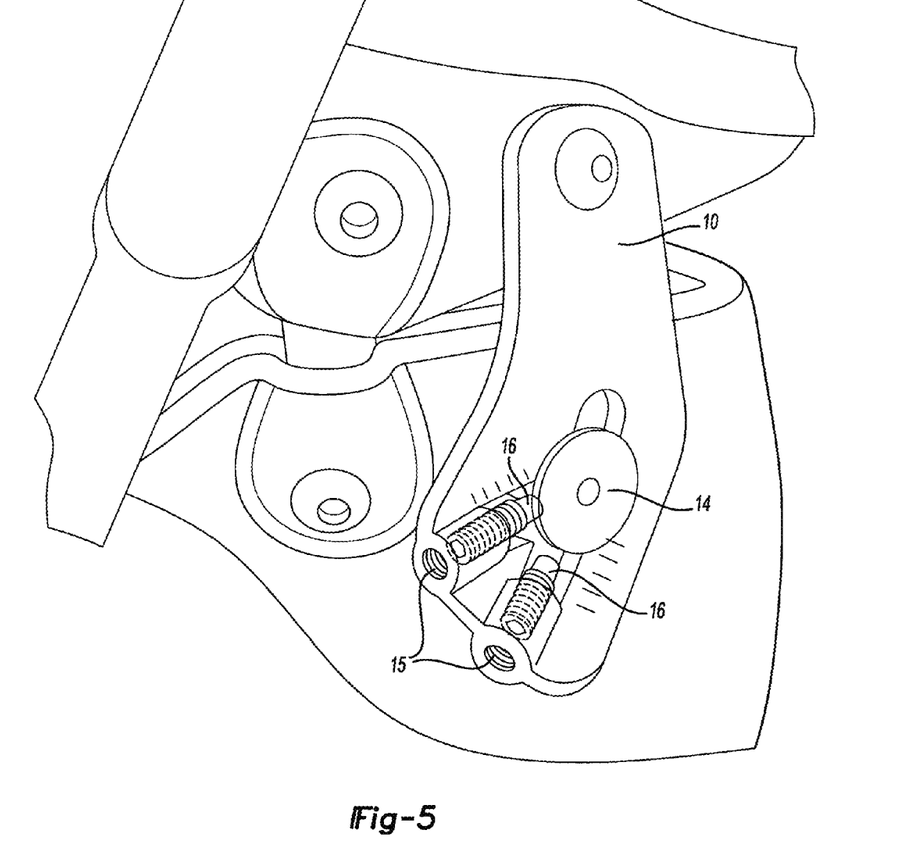
FIG. 5 shows the optional preferred design for the adjustable locking plate assembly (10), is further refined to include respective threaded bore engagement barrels (15), said locking engagement pin (14), locations for micro fine positioning screws (16), adjustments for the dorsi-flexion, and planter flexion positions of said pin (14), as well as the variable lock position of said Rooster Boot within the slotted plate assembly (10).
Figures 6, 7:
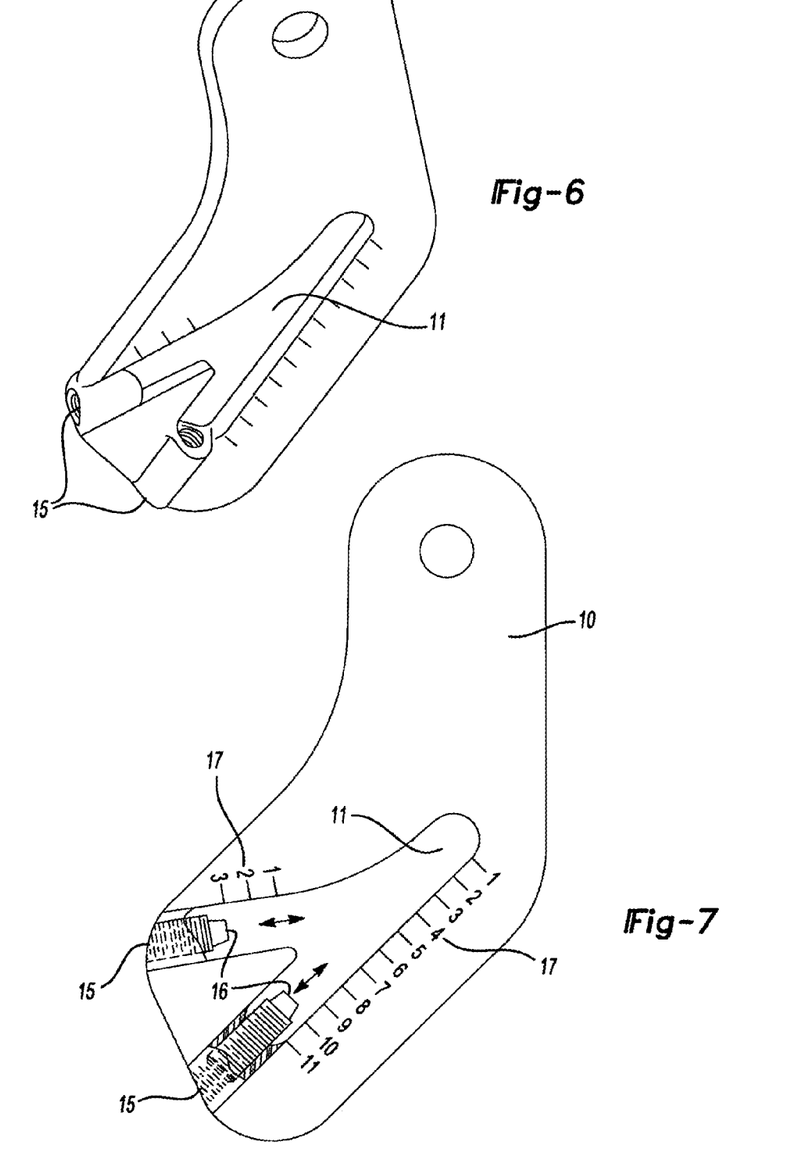
FIGS. 6 & 7 show exploded view illustrations of the adjustable locking plate assembly (10), and slot (11) threaded barrel (15) receiving bores for micro-fine engagement of the positioning screws (16).
Figure 8:
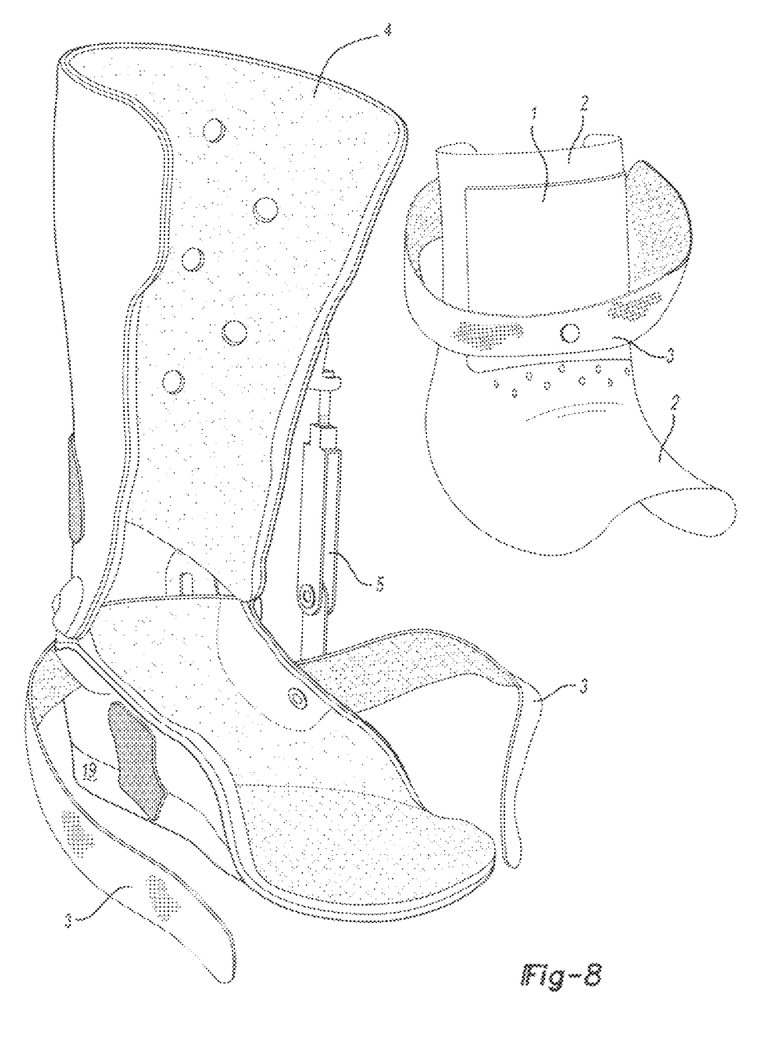
FIG. 8 is an exploded assembly view of the Rooster Boot design component novel features including; anterior pretibial shell and tongue assembly (2); anterior shell liner (1); posterior shell with liner (4); Velcro straps (3), and adjustable power pack assembly (5) (included for clarification and to assist Rooster Boot installation for the wearer); and a foot shell with liner (19) having a mid sole and sole.

The adjustable locking plate assembly (10), and slotted recess cutout (11), as shown in FIGS. 2-4; and further including the novel micro-fine adjustment features of the adjustable locking plate assembly (10), with receiving bores (15), and threaded engagement screws (16), and numerical readout indicia (17), as shown and depicted in FIGS. 5-7.

The adjustable features of the locking mechanism positioning plate with its micro-fine adjustments (FIGS. 5-7), enable the care giver to adjust in predetermined numerical readouts, for optimum range of motion control in dorsi and planter flexion. The Rooster Boot stabilizing force means provides an the adjustable memory power pack assembly readout with its micro-fine numerical readout positions, that enables the practitioner to optimize range of motion in the non-weight bearing mode while at rest, and well as in the weight bearing mode for therapy. The pre-tibial shell height may be increased or decreased accordingly, to attend to the patient's spasticity or muscle weakness. Also, additional static or dynamic straps may be utilized if needed for stability and control.

Additional second power pack assemblies, and second additional locking plate mechanisms could be incorporated in the Rooster Boot for optimal control over torsional and twisting conditions. However, in the preferred embodiment, the goal is to increase the patient's range of motion, thus preventing muscle shortening and contracture of the heal cord. The Rooster Boot preferred embodiment provides the optimum lightweight design for patient range of motion, foot alignment, and patient comfort. It is both simplistic in function with fine-tuned controls for the orthotic practitioner and parent while overcoming all the heavy and cumbersome alternate designs of the prior art.

What is claimed is:

1. An ankle foot orthosis having an upper leg portion and lower foot portion having lateral outside and medial inside portions comprising:
   an anterior pre-tibial shell and tongue assembly with an upper and lower portion;
   a posterior upper and lower base shell assembly comprising a posterior shell and a foot shell that are adapted to be moveable relative to each other by dorsi or plantar flexion of a wearer;
   an adjustable power pack assembly connected between said posterior shell and said foot shell and configured to provide a variable upward force on said foot shell; and
   a locking plate assembly interconnected with said posterior shell and said foot shell and configured to control a range of motion of said posterior shell and said foot shell relative to each other in dorsi and plantar flexion, said locking plate assembly comprising a plate mounted to said posterior shell and said foot shell, said plate including a slot with a pin being positioned within said slot, said pin configured to slide within said slot upon dorsi or plantar flexion of a wearer with said slot having ends configured to stop movement of said pin within said slot to thereby limit movement of said posterior shell and said foot shell relative to each other when worn by the wearer.

2. The ankle foot orthosis of claim 1, wherein the adjustable power pack assembly further includes an upper portion and a lower portion, and wherein said lower portion of said adjustable power pack assembly comprises a power band segment and said upper portion of said adjustable power pack assembly comprises a tension adjuster, and wherein said tension adjuster is configured to operatively adjust tension of said power band segment.

3. The ankle foot orthosis of claim 2, wherein said tension adjuster includes a threaded receiving bore engaged with a threaded bolt for adjusting the tension of said power band segment.

4. The ankle foot orthosis of claim 3, wherein said tension adjuster includes numerical indicia gradation inscriptions.

5. The ankle foot orthosis of claim 1, wherein the adjustable power pack assembly further includes an upper portion and a lower portion, and wherein said lower portion of said adjustable power pack assembly comprises a power band segment and said upper portion of said adjustable power pack assembly comprises a tension adjuster with a threaded receiving bore adapted to receive a threaded bolt, wherein said threaded bolt is configured to be rotated within said threaded receiving bore to adjust tension of said power band segment.

6. The ankle foot orthosis of claim 5, wherein the lower portion of said adjustable power pack assembly is secured to said foot shell and the upper portion of said adjustable power pack assembly is secured to said posterior shell.

7. The ankle foot orthosis of claim 1, further including a strap for securing the anterior pre-tibial shell and tongue assembly with the posterior upper and lower base shell assembly.

8. The ankle foot orthosis of claim 7, further including a pair of straps for securing the anterior pre-tibial shell and tongue assembly with the posterior upper and lower base shell assembly.

9. The ankle foot orthosis of claim 1, wherein said pin is mounted to said foot shell.

10. The ankle foot orthosis of claim 1, wherein the upper portion of said anterior pre-tibial shell and tongue assembly extends longitudinally upward with said posterior shell for weight bearing functional stability during walking and therapy.

11. The ankle foot orthosis of claim 1, wherein the adjustable power pack assembly includes a tension adjuster having a threaded receiving bore engaged with a threaded bolt for adjusting the force provided by said adjustable power pack assembly.

12. The ankle foot orthosis of claim 1, further including an additional adjustable power pack assembly and an additional locking plate assembly and wherein both the lateral outside and medial inside portions of the ankle foot orthosis are provided with an adjustable power pack assembly and a locking plate assembly for increased stability and torsional control.

13. The ankle foot orthosis of claim 1, wherein said slot is configured such that said pin can be positioned to retain said posterior shell and said foot shell in an approximately 90 degree orientation relative to each other.

14. An ankle foot orthosis having an upper leg portion and lower foot portion having lateral outside and medial inside portions comprising:
   an anterior pre-tibial shell and tongue assembly with an upper and lower portion;
   a posterior upper and lower base shell assembly comprising a posterior shell and a foot shell that are adapted to be moveable relative to each other by dorsi or plantar flexion of a wearer;
   an adjustable power pack assembly connected between said posterior shell and said foot shell and configured to provide a variable upward force on said foot shell; and
   a locking plate assembly interconnected with said posterior shell and said foot shell and configured to control a range of motion of said posterior shell and said foot shell relative to each other in dorsi and plantar flexion, said locking plate assembly comprising a plate mounted to said posterior shell and said foot shell, said plate including a slot with a pin being positioned within said slot, said pin configured to slide within said slot upon dorsi or plantar flexion of a wearer with said slot configured such that said pin can be positioned to stop movement of said pin within said slot and thereby stop movement of said posterior shell and said foot shell relative to each other.

15. The ankle foot orthosis of claim 14, wherein said slot is configured such that said pin can be positioned to stop movement of said posterior shell and said foot shell relative to each other in both a dorsi flexion position and a plantar flexion position.

16. The ankle foot orthosis of claim 15, wherein said slot is further configured such that said pin can be positioned to retain said posterior shell and said foot shell in an approximately 90 degree orientation relative to each other.

17. An ankle foot orthosis having an upper leg portion and lower foot portion having lateral outside and medial inside portions comprising:
   an anterior pre-tibial shell and tongue assembly with an upper and lower portion;
   a posterior upper and lower base shell assembly comprising a posterior shell and a foot shell that are adapted to be moveable relative to each other by dorsi or plantar flexion of a wearer;
   an adjustable power pack assembly connected between said posterior shell and said foot shell and configured to provide a variable upward force on said foot shell, wherein the adjustable power pack assembly further includes an upper portion and a lower portion, and wherein said lower portion of said adjustable power pack assembly comprises a power band segment and said upper portion of said adjustable power pack assembly comprises a tension adjuster, and wherein said tension adjuster is configured to operatively adjust tension of said power band segment; and a locking plate assembly interconnected with said posterior shell and said foot shell and configured to control a range of motion of said posterior shell and said foot shell relative to each other in dorsi and plantar flexion, said locking plate assembly comprising a plate mounted to said posterior shell and said foot shell, said plate including a slot with a pin being positioned within said slot, said pin configured to slide within said slot upon dorsi or plantar flexion of a wearer with said slot configured such that said pin can be positioned in said slot to stop movement of said pin within said slot and thereby stop movement of said posterior shell and said foot shell relative to each other.

18. The ankle foot orthosis of claim 17, wherein said slot is configured such that said pin can be positioned to stop movement of said posterior shell and said foot shell relative to each other in both a dorsi flexion position and a plantar flexion position.

19. The ankle foot orthosis of claim 17, wherein said slot is configured such that said pin can be positioned to retain said posterior shell and said foot shell in an approximately 90 degree orientation relative to each other.

* * * * *